United States Patent
Zito, Jr.

(10) Patent No.: US 7,398,921 B2
(45) Date of Patent: Jul. 15, 2008

(54) USER-SPECIFIC DISPENSING SYSTEM

(76) Inventor: Arthur J. Zito, Jr., 760 Stacy Oak Ct., Millersville, MD (US) 21108-2538

( * ) Notice: Subject to any disclaimer, the term of this patent is extended or adjusted under 35 U.S.C. 154(b) by 459 days.

(21) Appl. No.: 10/990,595

(22) Filed: Nov. 17, 2004

(65) Prior Publication Data

US 2006/0106488 A1    May 18, 2006

(51) Int. Cl.
*G06F 7/08* (2006.01)
(52) U.S. Cl. .................. 235/381; 235/383
(58) Field of Classification Search ............ 235/381, 235/383; 705/14, 16
See application file for complete search history.

(56) References Cited

U.S. PATENT DOCUMENTS

| | | | |
|---|---|---|---|
| 4,915,205 A * | 4/1990 | Reid et al. ............ 194/205 |
| 4,982,346 A | 1/1991 | Girouard et al. |
| 5,231,568 A | 7/1993 | Cohen et al. |
| 5,267,171 A * | 11/1993 | Suzuki et al. ............ 700/234 |
| 5,373,440 A | 12/1994 | Cohen et al. |
| 5,482,139 A * | 1/1996 | Rivalto ............ 186/36 |
| 5,642,485 A * | 6/1997 | Deaton et al. ............ 705/14 |
| 5,735,742 A | 4/1998 | French |
| 5,857,175 A * | 1/1999 | Day et al. ............ 705/14 |
| 6,021,362 A * | 2/2000 | Maggard et al. ............ 700/234 |
| 6,182,857 B1 * | 2/2001 | Hamm et al. ............ 221/2 |
| 6,412,654 B1 * | 7/2002 | Cleeve ............ 221/7 |
| 6,520,544 B1 | 2/2003 | Mitchell et al. |
| 6,578,735 B1 * | 6/2003 | Mothwurf ............ 221/255 |
| 6,854,642 B2 * | 2/2005 | Metcalf et al. ............ 235/375 |
| 6,874,612 B1 * | 4/2005 | Uland ............ 194/212 |
| 2002/0013174 A1 | 1/2002 | Murata |
| 2002/0022998 A1 | 2/2002 | Onoue |
| 2002/0042744 A1 | 4/2002 | Kohl |
| 2002/0047020 A1 * | 4/2002 | Dudek ............ 221/9 |
| 2002/0056745 A1 | 5/2002 | De La Fuente |
| 2002/0065579 A1 | 5/2002 | Tedesco et al. |
| 2002/0077174 A1 | 6/2002 | Luciano et al. |
| 2002/0107610 A1 * | 8/2002 | Kaehler et al. ............ 700/232 |
| 2002/0147640 A1 | 10/2002 | Daniele et al. |
| 2003/0036425 A1 | 2/2003 | Kaminkow et al. |

(Continued)

FOREIGN PATENT DOCUMENTS

EP    1 426 905 A    6/2004

(Continued)

OTHER PUBLICATIONS

Robert Kazel, AMN News Staff, Robot Rep Latest Tactic in Generics Push, http://www.ama-assn.org/amednews/3005/01/31/bil20131.htm, Jan. 31, 2005.

(Continued)

*Primary Examiner*—Uyen-Chau N Le
(74) *Attorney, Agent, or Firm*—Alicia M. Passerin, Esq.; Cohen & Grigsby, P.C.

(57) ABSTRACT

The invention provides a system to physically dispense an item on-site from a dispenser whereby the item to be dispensed is selected by the system based on user-specific or item-specific information. In an embodiment, the system selects the dispensed item based on both user-specific and item-specific information. In another embodiment the invention comprises a system that activates gaming features in a gaming device based on user-specific information.

17 Claims, 3 Drawing Sheets

U.S. PATENT DOCUMENTS

| | | |
|---|---|---|
| 2003/0061098 A1 | 3/2003 | Meyer |
| 2003/0073479 A1 | 4/2003 | Wilson et al. |
| 2003/0097302 A1 | 5/2003 | Overhultz et al. |
| 2003/0186739 A1 | 10/2003 | Paulsen et al. |
| 2004/0024642 A1 | 2/2004 | Sidlo et al. |
| 2004/0033833 A1 | 2/2004 | Briggs et al. |
| 2004/0092311 A1 | 5/2004 | Weston et al. |
| 2004/0103028 A1 | 5/2004 | Littman et al. |
| 2004/0128197 A1 | 7/2004 | Bam et al. |
| 2004/0133466 A1 | 7/2004 | Redmond |
| 2004/0152520 A1 | 8/2004 | Shinoda |
| 2004/0152521 A1 | 8/2004 | Shinoda |
| 2004/0158489 A1 | 8/2004 | Rogers |
| 2006/0272976 A1* | 12/2006 | Pinney et al. ............... 206/466 |

FOREIGN PATENT DOCUMENTS

| | | |
|---|---|---|
| JP | 03006692 A * | 1/1991 |
| WO | WO 9718538 A1 * | 5/1997 |
| WO | WO 01/12035 | 2/2001 |

OTHER PUBLICATIONS

Julie Rawe, Sarah Sturmon Dale, Popping Pills Out of an ATM, http://www.time.com/time/archive,/preview/0,10987,1029873,00.html, Feb. 28, 2005.

Medvantx Product Overview (recieved from MedVantx, Inc. Apr. 7, 2005).

Medvantx Aligns with Major Health Plans to Build the First Generic Delivery Network, Medvantx Press Release, Mar. 1, 2005.

* cited by examiner

USER-SPECIFIC DISPENSING SYSTEM

BACKGROUND OF THE INVENTION

1. Field of Invention

This invention relates in general to systems and methods for on-site, automated dispensing of items to users based on user-specific information. The system and methods can also be applied to gaming devices in which a special feature is actuated and/or an item is dispensed based on user-specific information.

2. Description of the Prior Art

In general, the retail market continues to become more competitive. There are an increasing number of options for consumers in terms of where to shop and which items to purchase. At the same time, providing targeted samples to consumers is an effective method of marketing. Therefore, there exists a powerful need to direct consumers into appropriate store locations and/or to direct samples of products into the hands of a targeted consumer.

While promotional methods have existed for ages, e.g., sales coupons, targeted discounts, free items with purchase, no system or method has attempted an automated approach to targeted on-site sampling. To do so would require (1) pre-knowledge of the targeted consumer, also referred to as the "user" of the system, and (2) the actual dispensation of samples to said user based on that pre-knowledge. Such a system would differ from one that issues a coupon or other redeemable, such as a token, to a user based on user-specific information, in that said system would actually physically dispense the item to the user on-site, thereby removing the necessity of a redemption step.

Such a system would provide a novel method and system to provide automated, on-site sampling based on user-specific information. The system and method could incorporate RFID, bar code, or any other reader technology into an automated system that can be kept and maintained on a target site or maintained from a central site. Reader systems such as RFID tags, bar codes, and other conventional data reading methods are incorporated into a variety of devices ranging from monitoring systems to gaming devices. One example would be a grocery store chain issuing discounts to holders of a preferred customer card. The card may have information on it that is readable by a bar code reader. The system identifies the user by the information contained on the card and issues a discount, or tracks the consumers purchase history, and issues coupons based on said history. Another example is Bam et al.'s U.S. patent application Ser. No. 10/691,459 (Publication No. US 2004/0128197), which discloses an electronic promotion system that sends coupons to targeted consumers, the coupons tailored to the specific consumer's profile. The consumer then may redeem said coupons at some future time.

Another example of the prior art is Meyer's U.S. patent application Ser. No. 10/245,149 (Publication No. US 2003/0061098 A1), which discloses a system that encourages consumers to patronize a particular business by awarding a prize or a discount to randomly selected consumers. But the system disclosed in Meyer's patent application does not physically dispense a sample. Another drawback of this system is that a dispensed item may not meet the needs or desires of the actual user because the dispensed item is not customized to that user's individual characteristics or preferences. Such a system is not necessarily based on user-specific information but rather simply rewards consumers that have a card.

Thus, there is a need for a system that both physically provides the item on-site from the dispenser unit itself and one that dispenses an item that is user-specific based on the particular user's characteristics.

SUMMARY AND OBJECTS OF THE INVENTION

In general, the dispensing system of the present invention comprises a user-identifier, such as an RFID tag or a bar code, containing information associated with a user. The system also comprises a reader that is capable of reading the user-identifier. The system has a processor that is capable of executing instructions to actuate dispensing means that in turn dispenses an item to the user. In this way, the system is designed to dispense an item that is appropriate for the user based on user-specific information.

In an alternate embodiment, the system is capable of conveying information associated with the items. In this alternate embodiment, the processor is capable of instructing an actuator to dispense items based on item-specific information. Item-specific information includes, but is not limited to, the number of items dispensed from at least one storage compartment or the weight of items remaining in at least one storage compartment.

In another embodiment, the invention comprises a system incorporated into a gaming device. Instead of dispensing a sample, the system will actuate at least one gaming feature based on the information associated with the identified user. This embodiment is designed to actuate a gaming feature that is appropriate for the user based on the user-specific information.

All embodiments may be optimally coupled with any device that dispenses a service or item in exchange for currency or other monetary means, such as a credit card.

It is therefore an object of the present invention to provide a system to physically dispense a sample item on-site to a user based on user-specific information.

It is a further object of the present invention to provide a system that physically dispenses an item on-site to a user based on information related to the items remaining in the system.

It is also an object of the invention to provide a gaming system that activates gaming features based on user-specific information.

It is a further object of the invention to provide a system that activates features within an existing gaming machine based on user-specific information.

It is still a further object of the invention to provide targeted automated sampling of items.

It is another object of the invention to provide a system to encourage consumer traffic to a location.

Other objects, features, aspects and advantages of the present invention will become better understood or apparent from the following detailed description, drawings, and appended claims of the invention.

DESCRIPTION OF THE PREFERRED EMBODIMENT

Figure 1:
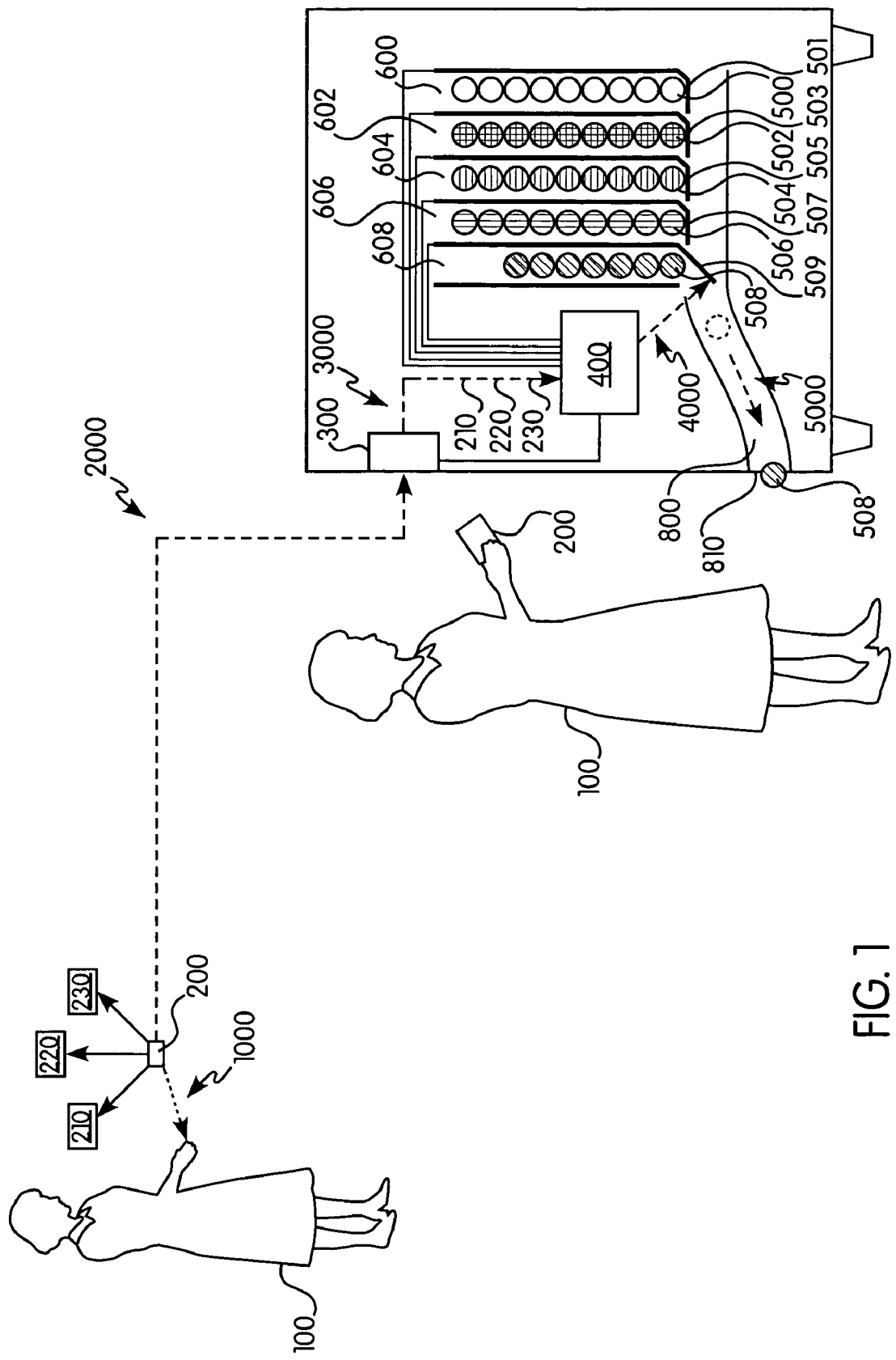
FIG. 1 is a schematic depiction of the user-specific dispensing system in an embodiment of the invention.

FIG. 1 shows a schematic depiction of an embodiment of the process and system for on-site dispensing of items based on user-specific information. In this embodiment, the system is schematically represented as a vending-type machine dispensing cylindrical items to a user. The skilled artisan will appreciate, of course, that there are a multitude of types of vending machines, many of which have differing mechanical or electrical configurations and capabilities. Thus, this embodiment of the invention is in no way limited to vending-type machines represented in this schematic. The skilled artisan will also appreciate, of course, that the dispensed items need not be cylindrical or be limited to any shape. The items could be intangible, such as a music clip. Thus, an item can be a physical sample or a service. Another example of an item as a service would be the system dispensing multi-media clip. Some of the other applications of the invention will become apparent from the schematic figures discussed below.

As shown in FIG. 1, a user 100 receives a user identifier 200. That step is represented as 1000. The way in which a user receives a card varies, but an example would be as follows: A vendor stationed at an event, for example, a sporting event, would solicit interested consumers and would gather information from the interested consumers. Such information could include the consumer's age, gender, sporting team or apparel preferences, location of residence, etc. The vendor would issue the user a card that could be used with the system. In this example, the card would be a user-identifier 200. Skilled artisans will appreciate that the user-identifier 200 need not be a card, for example, the user-identifier 200 could be any physical holder of information and need not be limited to any size or shape. Further, the user-identifier 200 could be any information that is specific to a user 100, which is inputted into the system, for example, the user 100 could enter the user's phone number into the system. Still further, the issuer of the user-identifier 200 need not necessarily be a vendor as is currently understood by the ordinary and accustomed meaning of "vendor." The user-identifier 200 comprises readable information that is specific to or is associated with the user. As stated above, said user-specific information may include gender, name, address, age, athletic preference, food preferences, music preferences, etc. FIG. 1 schematically represents such preferences as 210, 220, and 230. User-specific information 210, 220, and 230 on the user-identifier 200 may be in the form of a bar code or RFID information, but is not limited as such. User-specific information also includes information that a user is simply authorized to receive a sample. Therefore, information on a user-identifier that instructs the system to simply dispense an item is user-specific information.

Another step of the invention is represented by 2000. In this step, the user 100 presents the user-identifier 200 to the system. The system comprises a reader 300 capable of reading the coded information off of the user-identifier 200. In one example of an embodiment, the reader 300 is an RFID reader capable of reading data on a card that corresponds to the user's 100 age 210, gender 220, and soft drink preference 230. The reader 300 sends the user-specific data to a processor, the step being represented by 3000. In step 4000, the processor 400 is capable of processing the inputted user-specific data in order to instruct the system to dispense an item to a user, that item being selected based upon the user-specific data. The step of dispensing is represented by 5000. FIG. 1 depicts the item being dispensed as 508.

In some of the embodiments of the invention where the instructions are software, the software contains coded instructions, which translate the user-specific data into mechanical action of the system, specifically, mechanical actions of the dispensing means 501, 503, 505, 507, or 509. Software can also log the activities in a file. The software can validate whether the user-identifier 200 is authorized for activity. It can determine, for example, whether the user history warrants an item to be dispensed. The software can determine which type of item will be dispensed and log a tag number along with a time stamp and activity type to a file. A control code tag is able to retrieve the file and reset the system. Skilled artisans will appreciate that the invention is not limited or dependent upon any type of computer system, operating environment, architecture, or required to have a conventional computer to operate. As referred to above, in other embodiments of the invention, it is possible to reduce the software routine to a dedicated chip, and remove the typical computer components from the invention completely.

The step of the reader 300 being provided with the user-specific information 210, 220, and 230 of the user-identifier 200 to the processor 400 is represented by 3000. Once the processor accepts the user-specific data 210, 220, and 230, it executes an instruction to actuate a dispensing means 500, 502, 504, 506, 508 based on set instructions.

In this embodiment, the system has at least one compartment 600, 602, 604, 606 and 608, each of which stores a plurality of items to dispense. One such item is represented as 508. The invention is not limited to a type of item so long as the item is dispensed based upon user-specific data. However, presently such items may include toys, prizes, candy, soda, athletic gear, towels, etc. In the example shown in FIG. 1, each item is schematically represented, and each item is stored in its respective storage compartments 600, 602, 604, 606, and 608. In the preferred embodiment, the items meet a pre-selected set of characteristics appropriate for a user. That is, for example, if the user-specific information includes soda or candy preference, a soda or a candy item would be dispensed that corresponds to the preference.

Related to this aspect of the invention, other embodiments of the invention comprise dispensing an item based on whether the user 100 meets the pre-selected criteria selected by an entity wishing to promote certain goods. For example, the system could be located in a retail area such as a grocery store. The system may contain samples of after-shave, samples of a skin-toning product, and samples of vitamin supplements respectively. The pre-selected criteria may define that (1) males under forty five years of age are to receive after-shave samples; (2) females under forty-five years of age are to receive samples of the skin toning product; and that (3) all individuals over forty-five years of age will receive the sample of vitamin supplements. A twenty-nine year old male presenting his user-identifier to the system will cause the system to dispense to him a sample of after shave. In this way, the invention can provide for focused automated sampling, which is an important marketing tool. The invention also can drive consumer traffic to a location, which in this example, is a grocery store. In this embodiment, the steps of presenting 2000 the user identifier, reading the user-specific information 3000, and processing 4000 are the same as described above.

Dispensing 5000 is another aspect of the invention. The skilled artisan will appreciate that any conventional dispensing means can be used. Since the invention is not limited to any particular mechanical or electrical specifications, the dispensing means will depend largely on the type of unit the system is embodied within. In one embodiment, the dispensing means is a flange that is activated by a solenoid. The reader reads information contained on the user-identifier and sends the information to the processor, which processes instructions to send an electrical signal to the solenoid. This electrical signal charges a coil in the solenoid, which in turn pushes a rod mechanism in the solenoid to open the flange to dispense an item from the respective storage compartment—, for example into a dispensing chute 800, out of the opening 810, and on to the user 100. Alternate embodiments will use shooting solenoids to drive the sample into a dispensing chute ultimately accessible by the user.

In other embodiments, the invention has dimensions that are suitable for a retail shelf, for example, on the confectionery shelf of a convenience store; however, the size dimensions of the units are variable and could easily be adapted to any environment whether it be retail or service. The system could also be freestanding in a public place.

In another embodiment, the system could be installed or made a part of a jukebox type machine, or a machine that otherwise dispenses music or multimedia presentation. In such a system, the user-identifier would be presented to a reader on the system. The user-specific information would be sent to the processor. The processor would instruct the system to "dispense" or otherwise play a multimedia or music clip based on the user-specific information.

Figure 2:
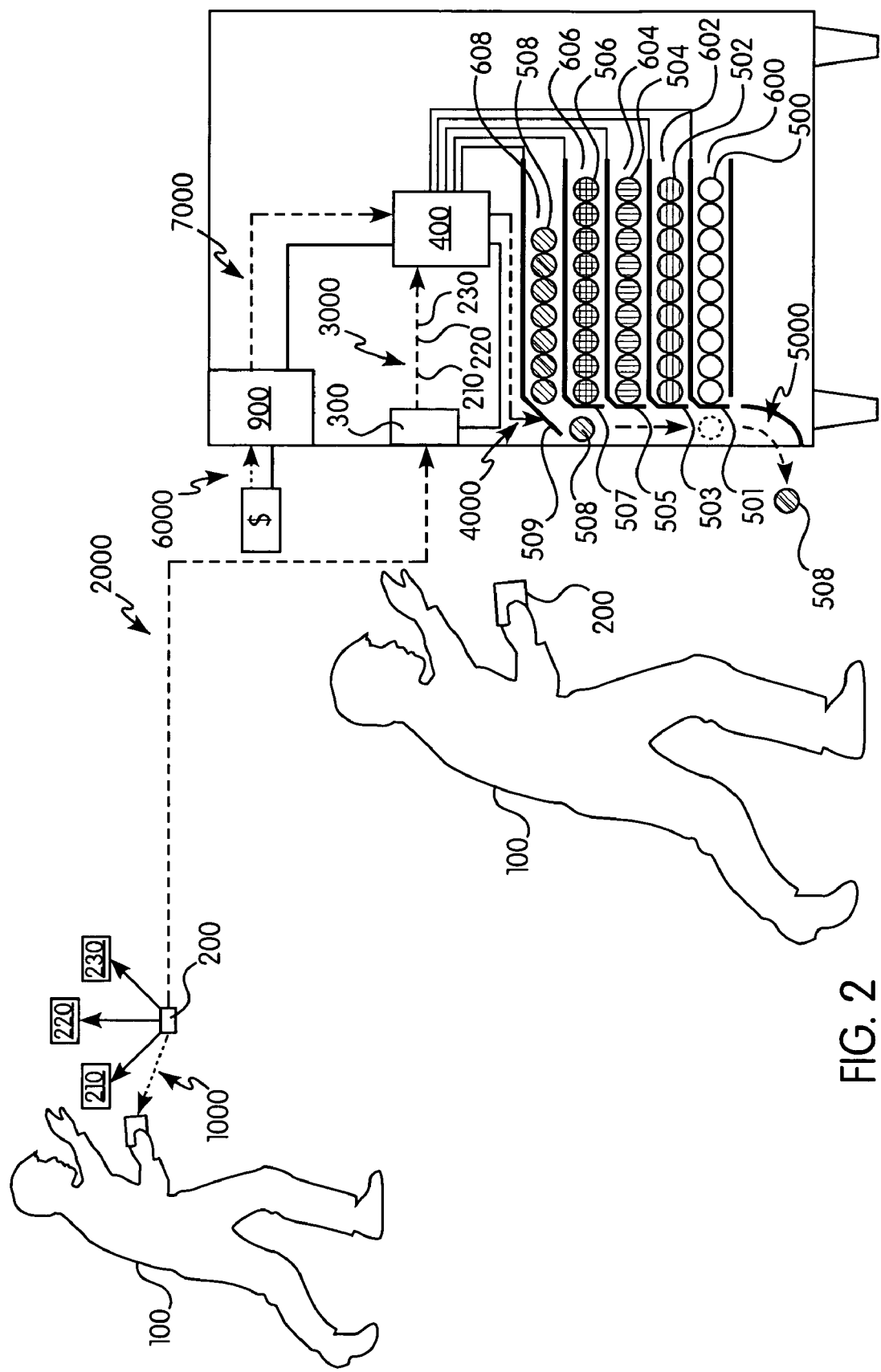
FIG. 2 is a schematic of another embodiment of the invention.

In an alternate embodiments shown in FIG. 2, the invention could be a dispensing or vending type system of the conventional type where the system is configured to accept currency and to dispense an item paid for by the user. A typical example of this would be a soda vending machine. In this alternate embodiment, the system contains a currency accepting means 900. The processor can contain and/or execute instructions to only activate the system if currency accepting means indicator to the process that the user 100 has paid for one of the items 508. For example, a user could purchase a soda by inserting currency into the currency acceptor 900 (the step represented as 6000), which would be communicated to the processor 400, represented by step 7000. In some embodiments, the processor 400 executes instructions to output a prompt to the user. In a preferred embodiment, the prompt would be a graphical display indicating to the user to present his or her user-identifier 200. The system then reads the user-specific information 210, 220, and 230, and optionally, the user's 100 immediately previous purchase choice, and instructs the dispensing means (508 for example) to dispense a separate item to the user 100 based on the selected criteria for that user type and/or the user's 100 selection.

Other embodiments of the invention include a system to distribute items to a member of a health club, where the distributed items are chosen based on pre-selected athletic interests of the member, such as providing tennis balls to a member who has previously indicated an interest in playing tennis. Alternatively, the member of the athletic club may have purchased a premium service. The information regarding the premium service would be contained on the user-identifier and the system would dispense items based on the member's status and/or preferences.

Another embodiment comprises a system to distribute meals to school students based on pre-selected menu preferences.

The skilled artisan will appreciate that the components of the system can be used with any vending machine, amusement machine, slot machine, or any device that dispenses an item or service.

In another embodiment, the system dispenses items based on said user-specific information and item-specific information. In this embodiment, the system dispenses at least one item based on information associated with the items in at least one of the storage compartments. This item-specific information includes, but is not limited to, the number of items dispensed from at least one storage compartment, the number of items remaining in at least one storage compartment, or the weight of items remaining in at least one storage compartment. This sample-specific information is conveyed to the processor, which in conjunction with the programmed instructions is capable of translating the information into mechanical actions of the dispensing means as described above.

Another embodiment of the invention is utilized in a gaming device. A gaming device according to the present invention incorporates all or some of the elements described in the embodiments above, except that the primary "item" being "dispensed" is a gaming feature. Therefore, in this embodiment of the invention, the "dispense" is to be understood as the activation of a gaming feature.

The user-identifier, reader, and processor are the same as those described above in FIG. 1 except that in this example system, the processor executes programmed instructions to translate the user-specific information to activate at least one gaming feature based on user-specific information stored on user-identifier and read by reader. Activated gaming feature is appropriate for user based on user-associated information. Activation of gaming feature includes deactivation of the gaming feature. The instructions, which can be encoded in software or embedded in a chip in the processor, are capable of validating whether the user-identifier is authorized for activity, determining history of use of the gaming system by user, and determining if and which gaming feature 575 should be activated. The instructions in conjunction with computer memory means also maintains a log of information, including the user-identifier and user's usage history, such as time, points scored, and what gaming feature was activated. Any processor known to those skilled in the art may be used in the present invention without departing from the scope of the invention.

Figure 3:
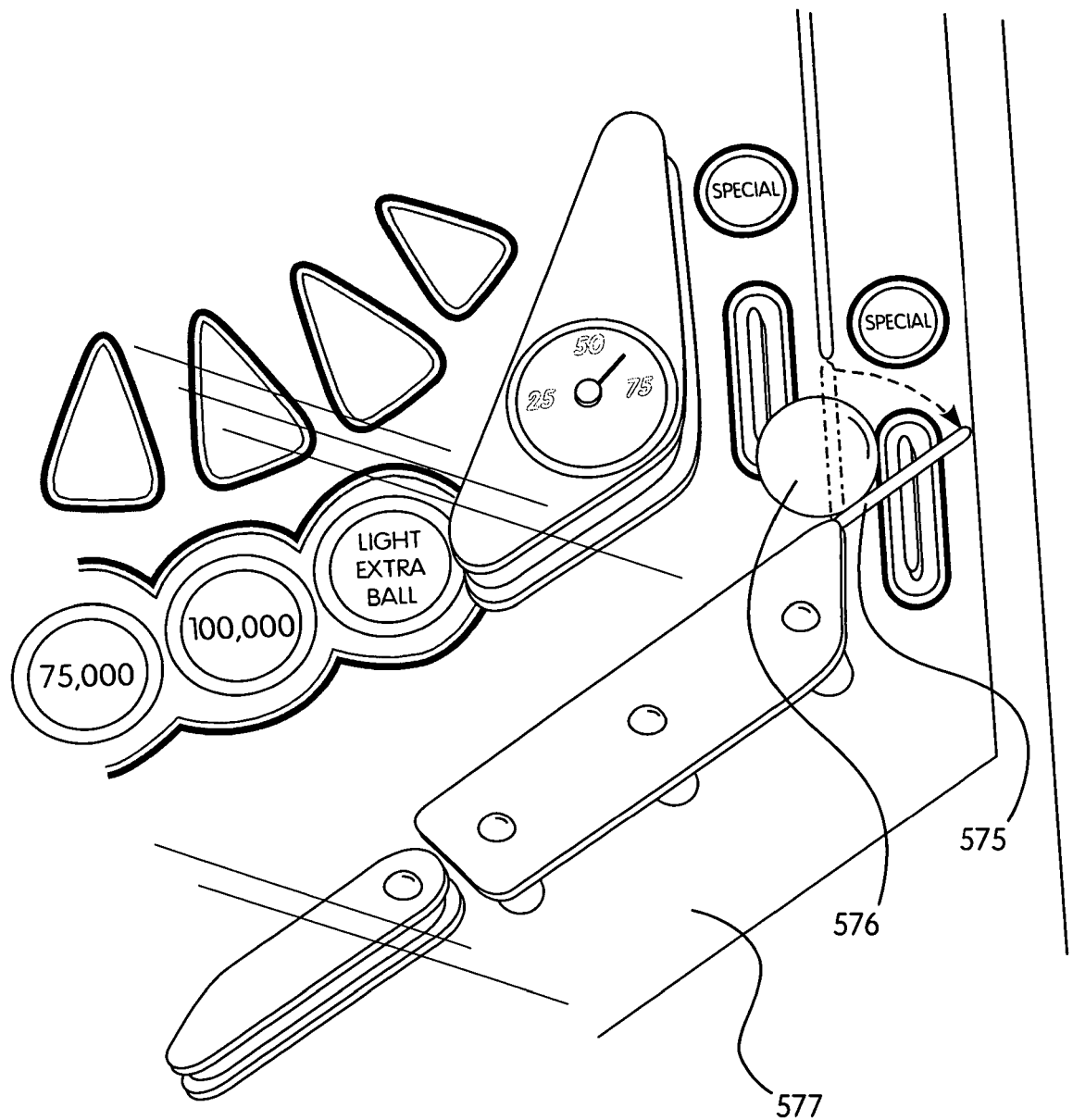
FIG. 3 is depiction of one embodiment of the invention incorporated into a gaming device.

In FIG. 3, the system is shown in conjunction with a pinball machine. A close-up view of the activated gaming feature 575, which is a gate in this example, is shown. Gaming feature 575 may be a feature that is not typically activated until user completes a sequence of flipper lane and ramp spinner switches. By activating gaming feature 575, the system provides easier play for a new or young user by blocking the outlane 577 where the pinball 576 could be lost.

Another example of the system involves video games. In this example, a user of the system may present her card to a video game having the system incorporated therein. The user could then be awarded specific advantages in the video game based on the user-specific information contained on her card.

In some embodiments, the gaming feature that is activated is a free game on the system. The gaming feature could also be an adjustment of the threshold necessary to reach a new level of the game or to obtain a re-play of the game.

While the foregoing has been set forth in considerable detail, it is to be understood that the drawings and detailed embodiments are presented for elucidation and not limitation. Design variations, especially in matters of shape, size and arrangements of parts may be made but are within the principles of the invention. Those skilled in the art will realize that such changes or modifications of the invention or combinations of elements, variations, equivalents or improvements therein are still within the scope of the invention as defined in the appended claims.

What is claimed is:

1. A system to dispense at least one user-appropriate item on-site, said system comprising:
   a. a readable user-identifier associated with a targeted user that stores information that is specific to said targeted user, wherein said information does not include a history of items purchased by said targeted user;
   b. a reader configured for reading said user-identifier;
   c. coded instructions to interpret said user-specific information read by said reader, automatically select at least one item of a plurality of items based on said user-specific information, and automatically actuate dispensation of said selected item to said targeted user without requiring further intervention from said targeted user;
   d. at least one storage means, said storage means configured for storing said plurality of items;
   e. at least one dispensing means coupled with respective at least one storage means configured for automatically dispensing said selected item from said storage means to said targeted user based upon said user-specific information read by said reader; and
   f. a processor coupled to said dispensing means and to said reader, said processor configured for executing said instructions to automatically actuate said at least one dispensing means to dispense said at least one selected item based upon said interpretation of said user-specific information,
   wherein said dispensation is not actuated by an item purchased by said targeted user and
   wherein said dispensed selected item is not a redeemable voucher.

2. The system of claim 1 wherein said system is incorporated into a vending machine.

3. The system of claim 1 further comprising a means configured for reading item-specific information coupled with said processor, and said processor further configured for executing said instructions to automatically actuate said at least one dispensing means to dispense said at least one selected item based upon information associated with items stored in said storage means.

4. The system of claim 3 wherein said item-specific information is a number of said items previously dispensed from at least one said storage means.

5. The system of claim 3 wherein said item-specific information is a number of said items remaining in at least one of said storage means.

6. The system of claim 3 wherein said item-specific information is a weight of said items remaining in at least one of said storage means.

7. The system of claim 1 wherein each of said dispensing means comprises a flange coupled with a solenoid, said solenoid coupled with said processor.

8. The system of claim 1 wherein each of said dispensing means comprises a shooting solenoid operable to accelerate said items out of the system.

9. The system of claim 1 wherein said information is said user's name.

10. The system of claim 1 wherein said information is said user's address.

11. The system of claim 1 wherein said information is said user's age.

12. The system of claim 1 wherein said information is said user's gender.

13. The system of claim 1 wherein said information is said user's personal characteristics.

14. The system of claim 1 further comprising a currency accepting means coupled with said processor, and said instructions further comprising instructions to activate said dispensing means upon the user inserting an appropriate amount of currency into said currency accepting means.

15. The system of claim 1 wherein said item is a service.

16. The system of claim 1 wherein said item is a music clip.

17. The system of claim 1 wherein said item is a multimedia clip.

* * * * *